US005614243A

United States Patent [19]

Dunn et al.

[11] Patent Number: 5,614,243
[45] Date of Patent: Mar. 25, 1997

[54] STARCH-BASED TEXTURIZING AGENTS AND METHOD OF MANUFACTURE

[75] Inventors: John M. Dunn, Sioux City, Iowa; Eugene T. Finocchiaro, Milton, Mass.

[73] Assignee: Opta Food Ingredients, Inc., Bedford, Mass.

[21] Appl. No.: 413,492

[22] Filed: Mar. 30, 1995

Related U.S. Application Data

[63] Continuation-in-part of Ser. No. 220,296, Mar. 31, 1994, abandoned.

[51] Int. Cl.$^6$ .................................. A23L 1/0522
[52] U.S. Cl. .................. 426/578; 426/565; 426/573; 426/575; 426/589; 426/605; 426/661; 426/804; 127/38; 127/55; 127/67; 127/71
[58] Field of Search .................. 426/573, 578, 426/575, 661, 589, 605, 804, 565, 582, 570, 583; 127/38, 55, 67, 69, 71

[56] References Cited

U.S. PATENT DOCUMENTS

| | | | |
|---|---|---|---|
| H1395 | 1/1995 | Prosser | 426/633 |
| 3,086,890 | 4/1963 | Sarko et al. | 127/69 |
| 3,238,064 | 3/1966 | Macarus et al. | 127/69 |
| 3,515,591 | 6/1970 | Feldman et al. | 127/32 |
| 3,650,770 | 3/1972 | Marcotta et al. | 99/139 |
| 3,658,552 | 4/1972 | Carlson et al. | 99/78 |
| 3,666,557 | 5/1972 | Jensen et al. | 127/32 |
| 3,836,677 | 9/1974 | Freck et al. | 426/103 |
| 3,962,465 | 6/1976 | Richter et al. | 426/48 |
| 3,986,890 | 10/1976 | Richter et al. | 127/38 |
| 4,187,326 | 2/1980 | Serafino et al. | 426/590 |
| 4,252,900 | 2/1981 | Muller et al. | 435/161 |
| 4,280,851 | 7/1981 | Pitchon et al. | 127/33 |
| 4,427,709 | 1/1984 | Guhl et al. | 426/578 |
| 4,452,978 | 6/1984 | Eastman | 536/111 |
| 4,499,116 | 2/1985 | Zwiercan et al. | 426/582 |
| 4,510,166 | 4/1985 | Lenchin et al. | 426/565 |
| 4,529,613 | 7/1985 | Mezzino et al. | 426/590 |
| 4,568,555 | 2/1986 | Spainer | 426/582 |
| 4,594,255 | 6/1986 | Wilson et al. | 426/578 |
| 4,608,265 | 8/1986 | Zwiercan et al. | 426/582 |
| 4,612,204 | 9/1986 | Huffman | 426/590 |
| 4,623,549 | 11/1986 | Katt et al. | 426/548 |
| 4,695,475 | 9/1987 | Zwiercan et al. | 426/582 |
| 4,705,691 | 11/1987 | Kupper et al. | 426/590 |
| 4,917,915 | 4/1990 | Cain et al. | 426/573 |
| 4,937,091 | 6/1990 | Zallie et al. | 426/582 |
| 4,956,193 | 9/1990 | Cain et al. | 426/573 |
| 4,971,723 | 11/1990 | Chiu | 252/315.3 |
| 4,992,539 | 2/1991 | Portnoy et al. | 536/120 |
| 5,051,271 | 9/1991 | Iyenger et al. | 426/658 |
| 5,089,171 | 2/1992 | Chiu | 252/315.3 |
| 5,108,773 | 4/1992 | Smith et al. | 426/582 |
| 5,128,156 | 7/1992 | McKenna et al. | 426/43 |
| 5,131,953 | 7/1992 | Kasica et al. | 127/65 |
| 5,180,604 | 1/1993 | Crane et al. | 426/582 |
| 5,194,284 | 3/1993 | Chiu et al. | 426/589 |
| 5,208,061 | 5/1993 | de Coninck et al. | 426/573 |
| 5,209,942 | 5/1993 | Bauer et al. | 426/573 |
| 5,215,778 | 6/1993 | Davison et al. | 426/582 |
| 5,250,316 | 10/1993 | Harris | 426/573 |
| 5,258,190 | 11/1993 | Cante et al. | 426/74 |
| 5,275,837 | 1/1994 | Eastman | 426/578 |
| 5,281,432 | 1/1994 | Zallie et al. | 426/549 |
| 5,286,510 | 2/1994 | Bauer et al. | 426/573 |
| 5,320,860 | 6/1994 | Duval et al. | 426/582 |
| 5,324,532 | 6/1994 | Stute et al. | 426/578 |
| 5,338,560 | 8/1994 | Wesdorp et al. | 426/573 |
| 5,387,426 | 2/1995 | Harris et al. | 426/573 |
| 5,395,630 | 3/1995 | Gamay | 426/42 |
| 5,424,088 | 6/1995 | Christianson et al. | 426/578 |
| 5,470,391 | 11/1995 | Mallee et al. | 127/38 |

FOREIGN PATENT DOCUMENTS

| | | | |
|---|---|---|---|
| 2047266 | 7/1991 | Canada | A25C 11/02 |
| 0120498 | 10/1984 | European Pat. Off. | A23C 20/00 |
| 298561A2 | 7/1988 | European Pat. Off. | A23L 1/307 |
| 0372184 | 9/1989 | European Pat. Off. | C12P 19/16 |
| 0366898 | 5/1990 | European Pat. Off. | C08B 30/14 |
| 519104A1 | 6/1991 | European Pat. Off. | A23L 1/0522 |
| 0441494 | 8/1991 | European Pat. Off. | A23D 7/00 |
| 0443844 | 8/1991 | European Pat. Off. | A23L 1/09 |
| 486936A1 | 11/1991 | European Pat. Off. | |
| 0480433 | 4/1992 | European Pat. Off. | A23L 1/325 |
| 512249A1 | 4/1992 | European Pat. Off. | A23L 1/0522 |
| 516107A1 | 5/1992 | European Pat. Off. | A23L 1/0522 |
| 0495407 | 7/1992 | European Pat. Off. | C08B 37/00 |
| 590203A1 | 9/1992 | European Pat. Off. | A23D 7/00 |
| 558832A2 | 11/1992 | European Pat. Off. | A23L 1/24 |
| 0529892 | 3/1993 | European Pat. Off. | A23C 1/09 |
| 551170A1 | 4/1993 | European Pat. Off. | |
| 0554818 | 8/1993 | European Pat. Off. | A23C 1/08 |
| 648425A2 | 4/1994 | European Pat. Off. | A23D 7/00 |
| 1279769 | 5/1970 | United Kingdom . | |
| 1430639 | 5/1973 | United Kingdom . | |
| 1562275 | 3/1980 | United Kingdom | C08B 31/00 |
| 89/12403 | 12/1989 | WIPO | A23L 1/10 |
| 91/02463 | 3/1991 | WIPO | A23L 1/0534 |
| 92/02147 | 2/1992 | WIPO | A23L 1/05 |
| 93/03630 | 3/1993 | WIPO | A23L 1/09 |
| 93/03629 | 3/1993 | WIPO | C08B 30/20 |
| 93/25084 | 12/1993 | WIPO | A23D 7/00 |
| 94/05163 | 3/1994 | WIPO | A23L 1/09 |
| 94/09645 | 5/1994 | WIPO | A23L 1/05 |

OTHER PUBLICATIONS

"Titanium Dioxide Dispersion", *Technical Data Bulletin* Warner Jenkinson Company, St. Louis, Missouri (6 pages).
Hullinger et al., "Food Applications of High Amylose Starches", *Food Technology* 27(3):22–24 (1973).
Int'l. Search Report, PCT/US94/11654.
Int'l Search Report, PCT/US95/04014.

*Primary Examiner*—Esther Kepplinger
*Assistant Examiner*—Lien Tran
*Attorney, Agent, or Firm*—Hamilton, Brook, Smith & Reynolds, P.C.

[57] ABSTRACT

A novel starch-based texturizing agent, methods of manufacture and food formulations containing the texturizing agent. The texturizing agent comprises an insoluble microparticle (e.g., titanium dioxide), a gum (e.g., xanthan gum) and starch (e.g., pregelatinized starch) in the form of a complex in which the insoluble microparticle has been stabilized or entrapped therein. The texturizing agent can be used in low fat and fat-free foods, including mayonnaise, edible spreads such as margarines, salad dressing, mousse, cottage cheese dressing, sour cream, ice cream, yogurt and cream cheese.

31 Claims, No Drawings

STARCH-BASED TEXTURIZING AGENTS AND METHOD OF MANUFACTURE

RELATED APPLICATION

This is a continuation-in-part of U.S. patent application Ser. No. 08/220,296, Mar. 31, 1994, now abandoned. The entire teachings of the application is incorporated herein by reference.

BACKGROUND

The health advantages of a diet low in fat are well documented. Attempts to formulate low-fat versions of food products that typically contain a high percentage of fat are made difficult due to the many functional roles that fats play in foods. Removal of fat from a food often leads to negative effects on structure and organoleptic properties such as smoothness, flavor profile, opacity, lubricity, etc. The consumer demand for low-fat foods that retain the quality of the corresponding full-fat formulation has led to the development of a large number of potential texturizing agents and fat replacers based on proteins, polyesters, and a variety of other approaches.

Several examples of fat replacers derived from starch include: a partially debranched starch used for providing fat-like texture, forming opaque clouds and producing thermoreversible gels (EP Application 0 372 184 A1 and U.S. Pat. No. 4,971,723 issued to Chiu); cold-water soluble and pregelatinized converted starches (by acid, enzyme or oxidation treatment) for use as fat or oil replacement in ice cream and mayonnaise (U.S. Pat. No. 4,510,166 issued to Lenchin et al.); enzyme-hydrolyzed thermoreversible starch gels as fat substitutes in mayonnaise, cream cheese, whipped cream and meat applications (U.S. Pat. Nos. 3,962,465 and 3,986,890 issued to Richter et al.); aqueous dispersion of granular starch hydrolysate (EP Application 0 443 844 A1 issued to Chiou et al.); macrocolloid carbohydrate particles for use in ice cream, yogurt, salad dressings, mayonnaise, coffee whitener and sour cream (PCT Application WO 89/12403 to Singer et al.); two-phase protein and carbohydrate fat substitute for use in salad dressings and cookie fillings (EP Application 0 441 494 A1 to Reimer); fat substitute comprising hydrated alginate and a complex carbohydrate (PCT Application WO 92/02147 to Shemer and Shemer); mixture of heat treated microcrystalline cellulose and xanthan gum used as a fat mimetic in frozen desserts and viscous and pourable salad dressings (PCT Application WO 91/02463 to Baer et al.); and insoluble modified starch used as a bulking agent, filler or texturizing agent in low-fat formulations (U.S. Pat. No. 5,051,271 issued to Iyengar et al.).

A number of methods have been developed to modify starches for use in food formulations and include: subjecting defatted amylose containing starch to high temperature and shear to disrupt the starch granules thereby producing a gel (U.S. Pat. No. 3,666,557 issued to Jensen and Long); cooking high amylose starch at 140°–170° C. to produce a solubilized cold water dispersible starch (U.S. Pat. No. 3,515,591 issued to Feldman et al.); cooking high amylose starch under shear at a temperature higher than the gelatinization temperature to produce a yellow gel (U.S. Pat. No. 3,836,677 issued to Freck et al.); and subjecting high amylose starches to a jet cooking/spray drying process to produce a pregelatinized starch (E.P. Application 0 366 898 A1 and U.S. Pat. No. 5 131 953 issued to Kasica and Eden).

SUMMARY OF THE INVENTION

The present invention pertains to a starch-based texturizing agent, to methods of manufacture and to food and non-food formulations containing the texturizing agent, particularly low fat and non-fat foods. The texturizing agent is a complex comprising an insoluble microparticle, a gum and starch. In one embodiment, the starch will be in the form of a pregelatinized starch; the insoluble microparticle is titanium dioxide; and the gum is xanthan gum. In another embodiment, the texturizing agent comprises a complex of starch and gum (e.g., xanthan gum). Examples of foods that can be formulated with the novel texturizing agent include mayonnaise, edible spreads such as margarines, salad dressing, mousse, cottage cheese dressing, sour cream, ice cream, yogurt, cream cheese and other foods which require a texturizing agent. The texturizing agent can also be incorporated into non-food formulations such as cosmetics, lotions, creams (e.g., suntan lotion), drugs, plastics, paints, shellacs, varnishes, inks, paper and textiles.

It has been shown that incorporation of a gum, such as xanthan gum, into a starch complex enhances the textural properties of the starch, thus making it a suitable texturizing agent having fat-like rheology. These properties are further enhanced by the incorporation of insoluble microparticles into the starch/gum complex. Both the starch/gum and starch/gum/microparticle complexes have improved fat-like textural properties compared to starch alone or simple non-complexed admixtures of the starch, gum and optionally insoluble microparticles. The presence of titanium dioxide uniquely enhances the textural characteristics of the complex. The resultant complex is smoother, creamier and has a shorter texture. Thus, the novel starch/gum and starch/gum/microparticle complexes can be used as effective texturizing agents.

DETAILED DESCRIPTION OF THE INVENTION

The present invention is based upon the discovery that titanium dioxide, a traditional opacifying agent, when incorporated into a starch/gum matrix results in a complex that has unique texturizing properties. When added into food formulations, the titanium dioxide/starch/gum complex yields products that are smoother, creamier and have a shorter texture than similar foods containing other texturizing agents, such as modified and pregelatinized starches. These properties increase as the titanium dioxide content increases. Moreover, these texturizing properties are enhanced over starch/gum complexes and simple admixtures of titanium dioxide, starch and gum. It is believed that the unique texturizing properties are due to the presence of titanium dioxide particles which cause perforations in the continuous, "sheet-like" microstructure of the starch/gum matrix. It is likely that the perforated microstructure is responsible for the deformable, fat-like characteristics of the complex. Such perforations are not present in complexes containing only starch and gum.

Based upon these findings, the invention pertains to starch-based texturizing agents, to methods for producing the texturizing agents, and to food and non-food formulations containing the texturizing agents, particularly low fat and non-fat foods. In one embodiment, the texturizing agent comprises an insoluble microparticle, a gum and starch in the form of a complex in which the insoluble microparticle has been stabilized or entrapped therein. In another embodiment, the texturizing agent comprises a starch and gum complex.

For purposes of the present invention, the term "texturizing agent" will be used to describe products derived from high amylose (>30% amylose as determined by iodine binding) starch that have been processed under specific conditions of temperature, pressure and shear, and has a dextrose equivalent (DE) value for the starch component of less than about 5, with about 1.5 being preferred as determined by the Luff-Schoorl method, Procedure D52, Corn Industry's Research Foundation, 6th Edition.

The term "insoluble microparticle" is intended herein to mean microparticles that are insoluble in aqueous media. The preferred size is less than 5 microns, and optionally less than 1 micron.

The term "complex" is intended herein to mean an intimately associated relationship between the starch, gum and optionally the insoluble microparticle. For example, as shown by scanning electron microscopy (SEM), titanium dioxide particles are incorporated into and become part of the starch/gum matrix. SEM results also show that due to the incorporation of titanium dioxide particles into the starch, the microstructure of the starch/gum is disrupted. The disrupted structure is more deformable. SEM results of a starch/xanthan gum complex revealed a microstructure that is continuous. The deformability and degree of non-starchy properties increases as the amount of insoluble microparticle increases.

The starch complex will contain an insoluble microparticle. Examples of suitable microparticles include aqueous insoluble inorganic and organic compounds, such as, but not limited to titanium dioxide, magnesium salts, barium salts, calcium salts (e.g., carbonates, sulfates, citrates, oxides). Microcrystalline cellulose, whey proteins and prolamines can also be used as the insoluble microparticle. Titanium dioxide is preferred. The insoluble microparticle can be incorporated into a starch/gum matrix under specific conditions before the starch is non-retrograded. The preferred amount of titanium dioxide will be from about 2 to about 25 percent by weight, with about 3 percent being most preferred. It is shown herein that as the amount of titanium dioxide increases, the overall textural properties of the complex is enhanced while its starchy mouthfeel is decreased. For other insoluble microparticles, the preferred amount is from about 5 to about 50 percent by weight.

The complex will also contain a gum, such as but not limited to xanthan gum, guar gum, gum arabic, carrageenan, locust bean gum and combinations thereof. The preferred gum is xanthan gum. The amount of xanthan gum added to the starch is from about 2 to about 10 percent by weight, with from about 5 to about 6 percent by weight being preferred.

The starch component will preferably be in the form of pregelatinized starch. Processes for making the starch component have been described in detail in PCT/US94/11654, filed Oct. 14, 1994, and U.S. patent application Ser. No. 08/138,541, filed Oct. 15, 1993, now U.S. Pat. No. 54,70391 which is a continuation-in-part of U.S. Ser. No. 07/900,899, filed Jun. 13, 1992, now abandoned to Francis M. Mallee and Eugene Terry Finocchiaro. The teachings of these applications are incorporated herein by reference in their entirety.

According to the method of this invention, texturizing agents are prepared from a high amylose starch which contains greater than about 30% amylose, and preferably about 70% amylose as determined by the iodine binding method. The high amylose starch can be obtained from a variety of plant sources, including but not limited to peas, oats, corn and barley. In addition, the high amylose starch can be chemically modified, for example by succinylation or crosslinking using known techniques. The starting material may be a product of the milling of whole grains in which the non-starch components of the grain have been removed. The milled starch product may be obtained in a wet or dry form. A number of commercial sources of high amylose starch include AMYLOMAIZE® VII (approx. 70% amylose; American Maize Products Co., Hammond, Ind.) and HYLON® VII (National Starch and Chemical Co., Bridgewater, N.J.). Filtering by treatment with diatomaceous earth and activated charcoal, as described below, results in removal of the fat and protein, thereby yielding texturizing agents with improved sensory properties.

The method for producing the novel texturizing agents generally involves: cooking the slurry under conditions of time, temperature, pressure, pH, ionic strength and shear sufficient to solubilize the starch by fully disrupting the starch granules while minimizing generation of objectionable side products which contribute off-flavor and off-color; filtering the solubilized starch to remove a substantial portion of non-starch components such as lipid and protein, preferably by treatment with diatomaceous earth and activated charcoal; adding a gum and optionally an insoluble microparticle (depending upon the final texturizing agent desired) under controlled conditions of temperature and shear; optionally homogenizing the filtrate; and cooling of the fully solubilized starch under controlled conditions of time, temperature and shear to yield a thixotropic gel. The retrograded texturizing agent can be dried to reduce the moisture content to provide a free-flowing powder. Alternatively the filtered starch solution is cooled to a temperature and for a period of time sufficient to allow partial precipitation of the starch, thereby resulting in a partially retrograded texturizing agent. In both instances, the texturizing agents can be used directly in food formulations. The dry powder may be used directly or can be rehydrated prior to use. Each of these steps are discussed in detail below.

Specifically, the method involves preparing a starch slurry in an aqueous medium with a total high amylose starch content of from about 1 to about 30% (w/w) solids, preferably from about 5 to about 15% (w/w). For purposes of the present invention, "aqueous medium" is defined as water or a solution which is substantially water such as buffer, acid, base, salt, antioxidant, reducing agent, and/or chelating agent solutions or a blend of water with a miscible organic solvent, in an amount sufficient to inhibit oxidation of lipids present in the starch starting materials. It is preferred that the aqueous medium, such as water, be pretreated to remove any dissolved minerals. The starch may be hydrated at ambient temperature or after the aqueous medium has been heated.

The resulting slurry is transferred into an evacuated reactor vessel equipped with appropriate stirring device for agitation during the cooking of the starch slurry. The starch slurry is subjected to controlled conditions of time, temperature, pressure, pH, ionic strength and shear, to fully disrupt the starch granules and solubilize the starch. For the purposes of the present invention, the term "solubilize" refers to the absence of any detectable particulate matter, especially partially disrupted starch granules, when viewed under 200 to 400 fold magnification using a standard light microscope. The rate of heating, time duration at the final cook temperature (i.e., the temperature above the gelatinization temperature of starch), and shear rate in the reactor vessel affect the properties of the final product.

The slurry is typically heated from room temperature (approximately 22° C.) to from about 125° C. to about 150° C., with about 138° C. being preferred, under stirring over a time period which ranges from 40 to 120 minutes, preferably 60 minutes until starch granules are solubilized. Variations in initial temperature and rate of heating affect the properties of the final product even though the total time at 138° C. is essentially unchanged.

The final temperature of 138° C. for cooking of the starch is preferred to produce texturizing agents that possess smooth mouthfeel, high opacity, and acceptable organoleptic properties. The complete disruption and solubilization of the starch is monitored by periodic sampling of small aliquots from the reactor over time and examination of the slurry under magnification (e.g., 200 to 400x) for presence or absence of starch granules. The heating step is considered complete when essentially all the starch granules have dissolved. The importance of the final temperature used in the present invention is illustrated by the following comparison. High amylose starch was heated to a maximum temperature in the reactor of 121° C. for 8 hours in the absence of shear. Even though the cooking process is carried out for a much longer time period than that of the present invention, this lower temperature does not allow for complete solubilization and disruption of the starch granules resulting in a product that contains relatively large particulates that exhibit grittiness and poor mouthfeel when tasted directly. In contrast, the higher temperature used in the present process insures full disruption of the starch granules and solubilization of the high amylose starch which yield a much smoother product.

Removal of oxygen from the slurry is important to produce a product with minimal off-color and off-flavor, as ascertained by visual and sensory perception. It is preferred that the dissolved oxygen content be less than 1 ppm to ensure that off-flavors resulting from oxidation are not perceived upon tasting. For example, this can be achieved by subjecting the slurry to a vacuum, sparging with an inert gas such as argon or nitrogen using either a vented vessel or closed vessel, or any combination of techniques effective for removal of dissolved gases especially oxygen from the slurry, such as oxygen scavengers. Deaerating step is carried out for a period of time necessary to insure removal of the bulk of the dissolved gases typically up to one hour, preferably, ten minutes. Other approaches to reduce off-flavors and off-colors may include, either alone or in combination, near complete removal of non-starch components from the starting material, the addition of antioxidants, reducing agents and or chelating agents to the slurry, or washing of the final product with aqueous or organic solvents, among other generally known methods.

An alternative method of heating is to directly inject steam into the slurry, such as can be accomplished in a rapid heat-up device such as a jet cooker. Using a jet cooker or other rapid heat-up device, higher temperatures above the preferred range can be tolerated without affecting product properties if the contact time is sufficiently short. Generally, the temperature is raised up to about 160° C. and maintained at the elevated temperature for up to about ten minutes. Higher temperatures can be used for shorter time periods.

Regulation of pH is also important to the texturizing properties of the product and the stability of the insoluble microparticle, such as titanium dioxide, in the starch complex. According to the methods of this invention, the typical pH of the slurry before and after cooking is in the range from about 3.0 to about 7.0, and preferably from about 4.3 to 4.7. The acidity of the slurry is controlled using appropriate food or cosmetic grade acidulants and alkali. The method of cooking will dictate the pH at which the starch is cooked. If a jet cooker is used, then the pH should be lower than that required for batch cooking.

Upon complete disruption of the starch granules and solubilization of the starch, the starch solution is cooled to a temperature below boiling and above about 85° C. with 100° C. being preferred. Temperatures lower than about 85° C. will result in inefficient filtration as the starch retrogrades. Cooling can be accomplished by any suitable means such as heat exchanger, flash cooling or by running cooling water through the reactor jacket. The cooled starch solution is then transferred from the reactor vessel by expulsion under pressure, pumping, or other suitable method.

The starch solution (at approximately 90° C.) is filtered to remove undissolved impurities, such as protein, fats and other compounds. Any filtration device having metal sieves, ceramic filters or membranes, filter papers/cloths, filter pads or other filter media can be used. For example, plate and frame filter presses, cartridge, bag and pressure leaf filters can be used. It is desirable to preheat the filters and filtering device to the temperature of the slurry to be filtered prior to filtration. This will prevent premature retrogradation of the starch on the filter media and consequent blinding of the filter.

The filtration step is preferably performed by filtering the solution through a secondary carbon-containing filter such as a filter fitted with activated charcoal impregnated pads or a filter fitted with a cartridge containing activated charcoal. In a preferred embodiment, a filter aid such as diatomaceous earth is typically added to the starch solution and stirred for about ten to about 120 minutes, with 60 minutes being preferred. The amount of diatomaceous earth used is generally from about 5% to about 20% by weight of the starch being purified, and is preferably about 10% by weight. The starch solution is then passed through a primary filter to remove the diatomaceous earth and then through the secondary filter containing the activated charcoal impregnated pads. Suitable carbon impregnated pads are available, for example, from Alsop Engineering Co., Kingston, N.Y. (S-51, grade 230).

Alternatively, the filtration step is performed by treating the starch solution with activated charcoal. Activated charcoal is added to the reactor vessel for approximately from about 10 to about 120 minutes, with 60 minutes being preferred. Typically, the solution is simultaneously treated with a filtering aid such as diatomaceous earth, e.g. CELITE® (CELITE® Corp.). The amount of diatomaceous earth generally used is as described above. The starch solution containing suspended activated charcoal and diatomaceous earth is then filtered, as described above, to remove the charcoal and diatomaceous earth.

Starch based texturizing agents which have been treated with activated charcoal and diatomaceous earth have reduced protein and fat contents compared with starch based texturizing agents which have not undergone this treatment. By removing impurities from the starch solution which prevent retrogradation, filtration facilitates the retrogradation of the starch. In addition, treatment with diatomaceous earth and activated charcoal gives the resulting texturizing agent improved sensory properties such as flavor.

A gum (such as xanthan gum) and an insoluble microparticle (such as titanium dioxide) are added to the filtered starch solution at a temperature of from about 75° C. to about 95° C. under agitating conditions. The amount of gum added to the starch solution will be from about 2 to about 10 percent by weight of starch, with from about 5 to about 6 percent by weight being preferred. The order in which the insoluble microparticle and gum are added to the starch solution can vary. They may be added simultaneously or sequentially. It is preferred that the gum be added first, followed by addition of the insoluble microparticle. The filtered starch solution is collected in a receiving vessel.

A retrograded, non-retrograded or partially retrograded starch can be produced from the filtered starch solution, depending on how the solution is processed. Drying the filtered starch solution before the starch precipitates produces a non-retrograded starch. Allowing the solution to cool so that the starch precipitates yields a retrograded starch. Adjusting the temperature and time of precipitation so that the starch only partially precipitates results in a partially retrograded starch.

A retrograded starch is produced by cooling the filtered or treated starch solution to a temperature sufficient to allow the starch to precipitate, typically from about 1° C. to 7° C. preferably to about 4° C. Optionally, salts suitable for use in food such as sodium chloride can be added to increase the rate of crystallization. Cooling should be carried out with a minimum of shear for maximum gel strength in the resultant precipitated texturizing agent; however, application of shear during the cooling step can be used to produce texturizing agents with varied functional properties, i.e., lower viscosity. For example, the filtrate can be stored in a temperature controlled cooler overnight. Alternatively, any efficient method of cooling can be used, such as, but not limited to jacketed kettles, tube-n-tube heat exchanger, conventional heat exchanger, belt chiller and shell-n-tube heat exchanger. After completion of the cooling process, the resultant precipitate can be stored in the temperature range of from about 4° C. to about 50° C., preferably about 4° C. to about 22° C.

Optionally, the treated, filtered starch solution can be subjected to shear before being allowed to retrograde in order to improve the sensory properties of the product. Shear may be provided by piston, probe, jet, or valve homogenization (e.g., one and two stage), colloid milling, or similar technique. Conditions of shear will vary with the specific technique employed.

The final product is obtained by cooling to a temperature to fully gel the starch/gum/microparticle complex. The preferred temperature is about 4° C. Cooling should be carried out with a minimum of shear for maximum gel strength in the resultant gel; however, application of shear during the cooling step can be used to produce texturizing agents with varied functional properties, i.e., lower viscosity. Alternatively, any efficient method can be used to cool the gel. After completion of the cooling process, the resultant paste-like gel can be stored in the temperature range of from about 4° C. to about 50° C., preferably about 4° C. to about 22° C.

The texturizing agent, in the form of a paste, can then be used directly in food or non-food formulations or dried by an appropriate method to a white, free-flowing powder. The method of drying is chosen to preserve functionality and facilitate rehydration. Methods common to those skilled in the art can be used. For example centrifugal atomizers, pressure nozzles and two fluid nozzles can be used to atomize the starch gel. Any alternative drying methods can be used, such as, but not limited to drum drying and freeze drying.

The properties of the texturizing agent may be further modified by adding excipients such as sugars, maltodextrin that aid in rehydration, other starches, or other constituents such as gums, hydrocolloids, proteins, lipids, flavors, colors, etc. Preferred excipients are any hydrolyzed starch-based carbohydrate, with low DE maltodextrin being most preferred. Excipients that aid in the rehydration are not necessary if the resultant starch solution is used in wet form without prior drying and rehydration or if the dry powder is rehydrated under conditions of sufficient heat and shear to insure complete rehydration.

If an excipient or other additive is used, it can be added prior to or after the addition of the gum and microparticle. Preferably, maltodextrin as excipient will be added to the cooked starch prior to filtration and addition of the microparticle and gum.

The microstructure of a starch/gum/titanium dioxide product, as characterized by SEM, can be described as a continuous, "sheet-like" starch/gum network that is perforated with holes varying in their size and shape. The network is devoid of starch granules or granule fragments. The titanium dioxide particles are intimately incorporated into the starch/gum matrix. It is believed that the perforated "sheet-like" microstructure is responsible for the deformable, fat-like characteristics of the texturizing agent in its gel form. For the starch/xanthan gum product, the microstructure is a continuous "sheet like" network that does not contain perforations, as is seen with the starch/gum/titanium dioxide complex.

The texturizing agents of this invention function in full-fat foods or can fully or partially replace fat in a variety of food products which typically contain a high percentage Of fat in their formulation. Generally, the texturizing agent can be incorporated into food formulations at levels between about 0.1 and about 10%, preferably between about 2 and about 6% (w/v). Applications of the texturizing agents include mayonnaise, edible spreads such as margarines, spoonable and pourable salad dressings, mousse, cottage cheese dressing, sour cream, ice cream, yogurt, cream cheese, and other foods which require a texturizing agent. The fat-like attributes and stability are achieved without chemical modification of the starch. Sensory evaluation of certain foods containing the texturizing agent indicated a smooth mouthfeel, a non-starchy taste and a fat-like texture. As a result of these fat-like attributes, food formulations normally containing fat can now be made having reduced levels of fat approaching 100% reduction in certain formulations.

As shown in the example section, a low fat mayonnaise was prepared with starch/xanthan gum/titanium dioxide in the form of a complex and as a simple admixture of these ingredients. The product formulated with the complex was more fat-like in texture, less pasty and smoother in mouthfeel than the sample prepared with the admixture of ingredients. Similarly, a low fat ranch salad dressing containing the complex was superior in sensory attributes compared to a like dressing made with an admixture of starch, xanthan gum and titanium dioxide. Thus, complexation of the starch, gum and insoluble microparticle components is important to achieving a texturizing agent that can satisfactorily replace fat in foods to closely approximate their full-fat counterparts.

The texturizing agents function to provide structure, opacity, viscosity, stability, and acceptable organoleptic attributes with performance approximating the qualities of the full fat versions when used in reduced fat foods. The texturizing agents lack off-flavors, do not mask the foods inherent flavors when added to a food formulation. The texturizing agents of the present invention have been shown to function well with both laboratory and commercial plant processing schemes and equipment.

In addition to food applications, the texturizing agents of this invention can be incorporated into non-food formulations, including but not limited to cosmetics, lotions, creams, drugs, plastics, paints, shellacs, varnishes, inks, paper and textiles.

The invention will be further illustrated by the following examples which are not to be construed as limiting in any way. All weights and percentages are given below as weight/weight unless otherwise specified.

EXAMPLE 1

Pilot Scale Production of Texturizing Agent

METHOD 1

Quiescently Cooled

Two hundred and one and a half lbs (91.4 kg) of reverse-osmosis deionized (RODI) water was metered, red into a 30 gallon (114 L) reactor (Lee Kettles, Phillipsburg, N.J.) and heated to 46.7° C. Twenty five lbs (11.3 kg) of 70% amylose corn starch (AMYLOMAIZE VII starch®, American Maize Products Co., Hammond, Ill.) was weighed into the reactor. The final starch solids concentration was 10% (w/w). The reactor contents were agitated at 340 rpm using a LIGHTNIN™ Mixer (Lightnin Mixers, Rochester, N.Y.; Model V5S18 with an A-310 impeller). The pH of the suspension was adjusted to 4.41 using 15% phosphoric acid. The batch was heated from 46.7° C. to 105° C. in 16 minutes. The heating began with the vessel open to atmospheric pressure. The vessel was sealed by closing a vent valve when the product temperature reached 97° C. A sample of product was withdrawn through a sample port and the dissolved oxygen level was measured at 0.65 ppm. The temperature was then raised from 105° C. to 138° C. in 60 minutes and the product was held at 138° C. for 60 minutes. The product was then cooled from 138° C. to 95° C. in 9 minutes by circulating 7° C. chilled water through the reactor jacket. The product was maintained at 95° C. by again adding steam to the jacket and the reactor was opened. Seven and a half lbs (3.40 kg) of maltodextrin (MALTRIN® M040; Grain Processing Corp., Muscatine, Iowa) and 2.5 lbs (1.13 kg) of diatomaceous earth (CELITE®; CELITE® Corporation, Lompoc, Calif.) were added. The batch was held for 60 minutes before filtering through two filter presses in series. The first press (Model BT-240; Alsop Engineering Co., Kingston, N.Y.) was dressed with four 24" (61.0 cm) square filter pads (A10 filter media; Alsop Engineering Co., Kingston, N.Y.). The press had one 2-inch (5.08 cm) wide frame installed between two one-half inch (1.27 cm) wide filter plates. The second press (Alsop Engineering Co.) was dressed with three 13-inch (33.0 cm) square carbon filter pads (164OHC pads, Cellulo Corporation, Fresno, Calif.). The presses had been preheated by circulating 95° C. RODI water through them. The batch was pumped at 23.4 lb/minute (10.6 kg/min) through the filter presses and into a holding kettle. A 2% (w/w) solids xanthan gum (KELTROL™, Kelco Inc., San Diego, Calif.) solution was added to the starch-maltodextrin solution and mixed for 15 minutes in a high shear mixer (Likwifier, Breddo, Inc., Kansas City, Mo.). Titanium dioxide powder (KOWET™, Warner Jenkinson, St. Louis, Mo.) was added to the batch and mixed for 5 minutes. The xanthan gum and titanium dioxide were added at approximately 75°–85° C. The final solids content of the product was 79% starch-maltodextrin, 15% titanium dioxide and 6% xanthan gum. The product was then emptied from the mixer into five gallon (18.9 L) pails and placed in a 4° C. refrigerator. The product was removed from the refrigerator 16 hours later and diluted by the addition of 0.44 lbs of RODI water per lb of paste (0.20 kg/kg) and spray dried. The spray dryer (APV Crepaco, Tonawanda, N.Y.) inlet and exit air temperatures were 218° C. and 104° C. respectively.

EXAMPLE 2

Pilot Scale Production of Texturizing Agent

METHOD 2

Spray Dried Without Prior Gelation

Six hundred and seventy lbs (304 kg) of reverse-osmosis, deionized (RODI) water was metered into a 100-gallon (379 liter) reactor (Lee Kettles, Phillipsburg, N.J.) and heated to 43.6° C. Eighty four lbs (38.1 kg) of 70% amylose corn starch (AMYLOMAIZE VII starch®, American Maize Products Co., Hammond, Ill.) was weighed into the reactor. The final starch solids concentration was 10% (w/w). The reactor contents were agitated using a LIGHTNIN™ mixer (Lightnin Mixers, Rochester, N.Y.) Model V5S18 with an A-310 impeller at 340 rpm. The pH of the suspension was adjusted to 4.55 by adding 15% phosphoric acid. The batch was heated from 43.8° C. to 105° C. in 13 minutes. The heating began with the vessel open to atmospheric pressure. The vessel was sealed by closing a vent valve when the product temperature reached 97° C. The temperature was then raised from 105° C. to 138° C. in 60 minutes. The product was held at 138° C. for 60 minutes. The product was then cooled from 138° C. to 95° C. in 11 minutes by circulating 7° C. chilled water through the reactor jacket. The product was maintained at 95° C. by again adding steam to the jacket and the reactor was opened. Twenty five lbs (11.3 kg) of maltodextrin (MALTRIN® M040, Grain Processing Corp., Muscatine, Iowa) and 8.4 lbs (3.81 kg) of diatomaceous earth (CELITE®, CELITE® Corp., Lompoc, Calif.) were added. The batch was held for 60 minutes before filtering through a filter press. The press (Model BT-240, Alsop Engineering Co., Kingston, N.Y.) was dressed with six 24" (61.0 cm) square filter pads (AC-230 filter media, Alsop Engineering Co.). The press has one 2-inch (5.08 cm) wide frame and one-half inch wide frame installed between three one-half inch (1.27 cm) wide filter plates. The press had been preheated by circulating 95° C. RODI water through it. The batch was pumped through the filter press and into a holding kettle. Titanium dioxide powder (KOWET™, Warner Jenkinson, St. Louis, Mo.) and a 2% (w/w) xanthan gum (KELTROL™, Kelco, Inc., San Diego, Calif.) solution were added to the starch-maltodextrin solution and mixed in a high shear mixer (Likwifier, Breddo, Inc., Kansas City, Kans.). The solids content of the product was 6% xanthan gum, 15% titanium dioxide and 79% starch-maltodextrin. The product was fed to the spray dryer at approximately 95° C. The spray dryer (APV Crepaco, Tonawanda, N.Y.) inlet and exit air temperatures were 127° C. and 90° C., respectively.

METHOD 3

Cooling with a Low-Shear Heat Exchanger Prior to Spray Drying

Two hundred and fifty pounds (113 kg) of reverse-osmosis, deionized (RODI) water was metered into a 30 gallon (113 liter) reactor (Lee Kettles, Phillipsburg, N.J.) and heated to 43.5° C. Thirty-two pounds (14 kg) of 70% amylose corn starch (AMYLOMAIZE VII starch®, American Maize Products Co., Hammond, Ill.) was weighed into the reactor. The final starch solids concentration was 10% (w/w). The reactor contents were agitated using a LIGHTNIN™ mixer (Lightnin Mixers, Rochester, N.Y.) Model V5S18 with an A-310 impeller at 340 rpm. The pH of the suspension was adjusted to 4.5 by adding 15% phosphoric acid. The batch was heated from 43.5° C. to 105° C. in 15 minutes. The heating began with the vessel open to atmospheric pressure. The vessel was sealed by closing a vent valve when the product temperature reach 97° C. The temperature was then raised from 105° C. to 138° C. in 69 minutes. The product was held at 138° C. for 60 minutes. The product was then cooled from 138° C. to 95° C. in 13 minutes by circulating 7° C. chilled water through the reactor jacket. The product was maintained at 95° C. by again adding steam to the jacket and the reactor was opened. Nine and six-tenth pounds (4.4 kg) of maltodextrin (MALTRIN® M040, Grain Processing Corp., Muscatine, Iowa) and three and two-tenth pounds (1.5 kg) of diatomaceous earth (CELITE®, CELITE® Corporation, Lompoc, Calif.) were added. The batch was held for 60 minutes before filtering through a filter press. The press (Model BT-240, Alsop Engineering Co., Kingston, N.Y.) was dressed with four 24" (61.0 cm) square filter pads (AC-230 filter media, Alsop Engineering Co.). The press had one 2-inch (5.08 cm) wide frame and one one-half inch wide frame installed between three one-half inch (1.27 cm) wide filter plates. The press had been preheated by circulating 95° C. RODI water through it. The batch was pumped through the filter press and into a holding kettle. Titanium dioxide powder (KOWET™, Warner Jenkinson, St. Louis, Mo.) and xanthan gum (KELTROL™, Kelco, Inc., San Diego, Calif.) powders were added to the starch-maltodextrin solution and mixed in a high shear mixer (Likwifier, Breddo Inc., Kansas City, Kans.). The solids content of the product was 3% xanthan gum, 15% titanium dioxide and 79% starch-maltodextrin. The mixture was cooled in a concentric tube-in-tube heat exchanger. The cooling water temperature was regulated to maintain a 50° C. outlet product temperature. The cooled mixture was immediately fed into a spray dryer. The spray dryer (APV Crepaco, Tonanwanda, N.Y.) inlet and exit air temperatures were 149° C. and 128° C. respectively. A two-fluid nozzle (1/8J Setup 22B, Spraying Systems, Wheaton, Ill.) was used to provide the atomization of the starch mixture. Air served as the atomization fluid. The air pressure was regulated at 80 psig.

METHOD 4

Cooling in an Agitated Vessel Prior to Spray Drying

A portion of the titanium dioxide-xanthan gum-starch-maltodextrin mixture from Example 2, Method 3 was transferred at 90° C. to a 40 gallon kettle (Groen Div., Elk Grove Village, Ill.). The mixture was cooled while stirred with a swept-surface agitator to 50° C. The jacket temperature was regulated to maintain a 50° C. product temperature. The cooled mixture was fed into a spray dryer. The spray dryer (APV Crepaco, Tonanwanda, N.Y.) inlet and exit air temperatures were 154° C. and 121° C., respectively. A two-fluid nozzle (1/8J Setup 22B, Spraying Systems, Wheaton, Ill.) was used to provide the atomization of the starch mixture. Air served as the atomization fluid. The air pressure was regulated at 80 psig.

EXAMPLE 3

Pilot Scale Production of Texturizing Agents Prepared with either Calcium Citrate or Microcrystalline Cellulose in Lieu of Titanium Dioxide Six hundred and seventy lbs (304 kg) of reverse-osmosis, deionized (RODI) water was metered into a 100-gallon (379 liter) reactor (Lee Kettles, Phillipsburg, N.J.) and heated to 44.5° C. Eighty four lbs (38.1 kg) of 70% amylose corn starch (AMYLOMAIZE VII® starch, American Maize Products Co., Hammond, Ill.) was weighed into the rector.

The final starch solids concentration was 10% (w/w). The reactor contents were agitated using a LIGHTNIN™ mixer (Model V5S18, Lightnin Mixers, Rochester, N.Y.) with an A-310 impeller at 340 rpm. The pH of the suspension was adjusted to 4.56 by adding 15% phosphoric acid. The batch was heated from 42.0° C. to 105° C. in 14 minutes. The heating began with the vessel open to atmospheric pressure. The vessel was sealed by closing a vent valve when the product temperature reached 97° C. The temperature was then raised from 105° C. to 138° C. in 56 minutes. The product was held at 138° C. for 60 minutes. The product was then cooled from 138° C. to 95° C. in 12 minutes by circulating 7° C. chilled water through the reactor jacket. The product was maintained at 95° C. by again adding steam to the jacket and the reactor was opened. Twenty five lbs (11.3 kg) of maltodextrin (MALTRIN® M040, Grain Processing Corp., Muscatine, Iowa) and 8.4 lbs (3.81 kg) of diatomaceous earth (CELITE®, CELITE® Corp., Lompoc, Calif.) were added to the batch. The batch was filtered through two filter presses in series. The first press (Model BT-240, Alsop Engineering Co., Kingston, N.Y.) was dressed with six 24" (61.0 cm) square filter pads (A-10 filter media, Alsop Engineering Co.). The press had one 2-inch (5.08 cm) wide frame and one half inch (1.27 cm) frame installed between one-half inch (1.27 cm) wide filter plates. The second press (Alsop Engineering Co.) was dressed with five 13-inch (33.0 cm) square carbon filter pads (1640HC pads, Cellulo Corp., Fresno, Calif.). The presses were preheated by circulating 95° C. RODI water through them. The batch was pumped at 14.4 lbs/minute (6.51 kg/min) through the filter presses and into a holding kettle. A 2% (w/w) xanthan gum solution was added to the batch. The solids content of this batch was 7.06% xanthan gum and 92.94% starch-maltodextrin.

Calcium citrate prepared according to U.S. Pat. No. 5,194,270 was added to a portion of the starch-maltodextrin-xanthan solution and mixed in a high-shear mixer (Likwifier, Breddo, Inc., Kansas City, Kans.). The final product solids were then 79% starch-maltodextrin, 6% xanthan gum and 15% calcium citrate. The product was poured into a 5-gallon (18.9 liter) pail and placed into a 4° C. refrigerator. Twenty nine lbs (13.0 kg) of this product was diluted with 24.4 lbs (11.1 kg) of water and spray dried. Inlet and outlet air temperatures were 190° C. and 115° C., respectively.

Microcrystalline cellulose (RC-591F, FMC Corp., Philadelphia, Pa.) was added to a portion of the starch-maltodextrin-xanthan solution and mixed in a high-shear mixer (Likwifier, Breddo, Inc., Kansas City, Kans.). The final product solids were then 79% starch-maltodextrin, 6% xanthan gum and 15% microcrystalline cellulose. The product was poured into a 5-gallon (18.9 liter) pail and placed into a 4° C. refrigerator. Thirty lbs (13.5 kg) of this product was diluted with 25.4 lb (11.5 kg) of water and spray dried. Inlet and outlet air temperatures were 200° C. and 125° C., respectively.

EXAMPLE 4

Pilot Scale Preparation of Texturizing Agent Prepared from Precipitated Calcium Carbonate in Lieu of Titanium Dioxide Six hundred and seventy lbs (304 kg) of reverse-osmosis, deionized (RODI) water was metered into a 100-gallon (379 liter) reactor (Lee Kettles, Phillipsburg, N.J.) and heated to 46.4° C. Eighty four lbs (38.1 kg) of 70% amylose corn starch (AMYLOMAIZE VII®, American Maize Products Co., Hammond Ill.) was weighed into the reactor. The final starch solids concentration was 10% (w/w). The reactor contents were agitated using a LIGHTNIN™ mixer (Lightnin Mixers, Rochester, N.Y.) Model V5S18 with an A-310 impeller of 340 rpm. The pH of the suspension was adjusted to 4.58 by adding 15% phosphoric acid. The batch was heated from 46.4° C. to 105° C. in 13 minutes. The heating began with the vessel open to atmospheric pressure. The vessel was sealed by closing a vent valve when the product temperature reached 97° C. The temperature was then raised from 105° C. to 138° C. in 61 minutes. The product was held at 138° C. for 60 minutes. The product was then cooled from 138° C. to 94.8° C. in 10 minutes by circulating 7° C. chilled water through the reactor jacket. The product was maintained at 95° C. by again adding steam to the jacket and the reactor was opened. Twenty five lbs (11.3 kg) of maltodextrin (MALTRIN® M040, Grain Processing Corp, Muscatine, Iowa) and 8.4 lbs (3.81 kg) of diatomaceous earth (CELITE®, CELITE®Corporation, Lompoc, Calif.) were added. The batch was held for 64 minutes before filtering through two filter presses in series. The first press (Model BT-240, Alsop Engineering Co., Kingston, N.Y.) was dressed with six 24-inch (61.0 cm) square filter pads (A-10 filter media, Alsop Engineering Co.). The press had one 2-inch (5.08 cm) wide and one ½ inch (1.27 cm) wide frame installed between one-half-inch (1.27 cm) wide filter plates. The second press (Alsop Engineering Co.) was dressed with five 13-inch (33.0 cm) square carbon filter pads (1640HC pads, Cellulo Corporation, Fresno, Calif.). The presses had been preheated by circulating 95° C. RODI water through them. The batch was pumped through the filter presses into a holding kettle. A 2% solids (w/w) xanthan gum (KELTROL™, Kelco Inc, San Diego, Calif.) solution was added to the starch-maltodextrin solution and mixed for 15 minutes in a high shear mixer (Likwifier, Breddo Inc., Kansas City, Kans.). Precipitated calcium carbonate (USP Albaglos, Pfizer Specialty Minerals, Bethlehem, Pa.) was added to the batch and mixed for 5 minutes. The product solids were 79% starch-maltodextrin, 15% calcium carbonate, and 6% xanthan gum. A portion of the product was them emptied from the mixer into five-gallon (18.9 liter) pails and placed in a 4° C. refrigerator. The product was removed from the refrigerator 16 hours later and spray dried. The spray dryer (APV Crepaco, Tonawanda, N.Y.) inlet and exit air temperatures were typically 185° C. and 115° C. respectively. The remainder of the product was pumped through a tube-within-a-tube heat exchanger traced with 45° C. water and into the spray dryer to be dried. The product temperature feeding the dryer was 18° C. The spray dryer inlet and exit air temperatures for this product were typically 185° C., and 115° C., respectively.

EXAMPLE 5

Pilot Scale Preparation of Texturizing Agent Starch-Xanthan Gum Complex Without Titanium Dioxide)

Two hundred lbs (90.7 kg) of reverse-osmosis, deionized (RODI) water was metered into a 30-gallon (114 liter) reactor (Lee Kettles, Phillipsburg, N.J.) and heated to 48.5° C. Twenty five lb (11.3 kg) of 70% amylose corn starch (AMYLOMAIZE VII®, American Maize Products Co., Hammond Ill.) was weighed into the reactor. The final starch solids concentration was 10% (w/w). The reactor contents were agitated using a LIGHTNIN™ mixer (Lightnin Mixers, Rochester, N.Y.) Model V5S18 with an A-310 impeller at 340 rpm. The pH of the suspension was adjusted to 4.56 by adding 15% phosphoric acid. The batch was heated from 48.5° C. to 105° C. in 13 minutes. The heating began with the vessel open to atmospheric pressure. The vessel was sealed by closing a vent valve when the product temperature reached 97° C. A sample of product was withdrawn through a sample port and the dissolved oxygen level was measured at 0.50 ppm. The temperature was then raised from 105° C. to 138° C. in 60 minutes. The product was held at 138° C. for 60 minutes. The product was then cooled from 138° C. to 95° C. in 7 minutes by circulating 7° C. chilled water through the reactor jacket. The product was maintained at 95° C. by again adding steam to the jacket and the reactor was opened. Seven and a half lbs (3.4 kg) of maltodextrin (MALTRIN® M040, Grain Processing Corp, Muscatine, Iowa) and 2.5 lbs (1.13 kg) of diatomaceous earth (CELITE®, CELITE® Corporation, Lompoc, Calif.) were added. The batch was held for 60 minutes before filtering through two filter presses in series. The first press (Model BT-240, Alsop Engineering Co., Kingston, N.Y.) was dressed with four 24-inch (61.0 cm) square filter pads (A-10 filter media, Alsop Engineering Co.). The press had one 2-inch (5.08 cm) wide frame installed between two one-half-inch (1.27 cm) wide filter plates. The second press (Alsop Engineering Co.) was dressed with three 13-inch (33.0 cm) square carbon filter pads (1640HC pads, Cellulo Corporation, Fresno, Calif.). The presses had been preheated by circulating 95° C. RODI water through them. The batch was pumped through the filter presses and into a holding vessel. A 2% solids (w/w) xanthan gum (KELTROL™, Kelco Inc, San Diego, Calif.) solution was added to the starch-maltodextrin solution and mixed for 5 minutes in a high-shear mixer (Likwifier, Breddo Inc., Kansas City, Kans.). The product solids were 94% starch-maltodextrin and 6% xanthan gum. The product was then emptied from the mixer into five-gallon (18.9 liter) pails and placed in a 4° C. refrigerator. The product was removed from the refrigerator 16 hours later and diluted by the addition of 0.85 lbs of RODI water per lb of paste (0.386 kg/kg) and spray dried. The spray dryer (APV Crepaco, Tonawanda, N.Y.) inlet and exit air temperatures were 193° C. and 102° C., respectively.

EXAMPLE 6

Characterization of Texturizing Agent

A. Titanium Dioxide Assay

The titanium dioxide content of the texturizing agent was estimated by employing a total ash method that is applicable to starches, dextrins and other modified starches. Association of Official Analytical Chemists, *Official Methods of Analysis*, 13th Ed., Secs. 31, 102, p. 508; 31, 215, p. 534 (1980).

B. Gel Strength Method

The gel strength of the texturizing agent was determined by measuring the depth of penetration of a gel with a penetrometer. A gel (10% on a solid basis) of the texturizing agent was prepared by blending the appropriate amount of texturizing agent and water in a Waring blender at 92° C. at high speed for 5 minutes. The resultant slurry was poured into sample cups and held at 4° C. overnight. The gel strength was measured by placing the cup under a Precision Scientific Penetrometer (Petroleum Instruments Company, Bellwood, Ill., Model TS-73515 BA-3) and touching the 35 gram cone to the surface of the gel. The cone was dropped for 5 seconds and the distance fallen was measured in millimeters. The average was taken if more than one cup was collected per sample.

C. Brookfield Viscosity

Gels (3% on a solid bases; s.b.) of the texturizing agent were prepared by blending 4.8 grams (s.b.) texturizing agent and 156 grams of water in a Waring blender at 92° C. at high speed for 5 minutes. A gel (10% on a solid basis) of the texturizing agent was prepared by blending the appropriate amount of texturizing agent and water in a Waring blender at 92° C. at high speed for 5 minutes. The resultant slurry was poured into 160 ml beaker, covered and held at 4° C. overnight. Subsequently the viscosity was determined employing a Brookfield viscometer model DV–II+ (Stoughton, Mass.). To ensure homogeneity, the sample was first mixed with Brookfield spindle #2 at 100 rpm for 15 seconds. The spindle was changed to #6 and after shearing the sample for 30 seconds at 50 rpm, the measurement was recorded in Brookfield centipoise (cP).

D. Scanning Electron Microscopy

A gel (10% on a solid basis) of the texturizing agent was prepared by blending the appropriate amount of texturizing agent and water in a Waring blender at 92° C. at high speed for 5 minutes. The resultant slurry was poured into sample cups and held at 4° C. overnight. The gel sample was spread using a spatula onto a brass block which had been cooled with liquid nitrogen. Subsequent to freezing, the sample was fractured into 3–5 mm pieces using a razor blade which had been cooled in liquid nitrogen. The pieces were then stored in 100% ethanol at −10° C. for 12–18 hours and the ethanol was exchanged 3–5 times. Samples were then critical point dried using $CO_2$ as the transition fluid. Finally, samples were mounted on specimen stubs with colloidal graphite adhesive and sputter-coated with 15–25 nm gold-palladium (60:40). Samples were then imaged at between 1 and 10 kV using an AMR-1000 scanning electron microscope.

E. Characterization of Texturizing Agent

The texturizing agent prepared according to Example 1 was evaluated employing the methods described above in A through D above. The titanium dioxide content, which is responsible for enhancing texture as well as the opacifying strength of the texturizing agent, was 15.1% by weight. The gel strength and Brookfield viscosity were 16.3 mm and 1047 cP, respectively. The microstructure of the texturizing agent, as characterized by SEM, can be described as a continuous "sheet-like" starch/gum network that is perforated with holes varying in their size and shape. The network is devoid of starch granules or granule fragments and the titanium dioxide particles are intimately incorporated into the starch/gum matrix. It is likely that this perforated "sheet-like" microstructure is responsible for the deformable, fat-like characteristics of the texturizing agent in its gel form. Sensory evaluation of a 10% gel indicated a material that is smooth, lubricous and exhibits a deformable, non-starchy, fat-like texture.

In another experiment a series of texturizing agents were produced at varying concentrations of titanium dioxide ranging between 2% and 15%. The xanthan gum concentration was held constant at 6%. The rheological results clearly showed, as a function of increasing titanium dioxide concentration, that the gel strength decreased significantly, i.e., the penetration measurements were 11.2 mm and 15 mm for the 2% and 15% titanium dioxide samples, respectively. The sensory results for these samples showed a similar trend in that the yield stress also decreased as the titanium dioxide concentration increased. The overall textural preference also increased as a function of titanium dioxide concentration and was highest for the sample containing 15% titanium dioxide. The underlying sensory attribute that contributed most significantly to the increase in overall preference was the concomitant decrease in starchy texture.

EXAMPLE 7

Preparation of a Low-Fat Mayonnaise Containing Texturizing Agent

A low-fat mayonnaise was prepared with the texturizing agent produced in Example 1, using the following formula:

| Ingredients | Weight Percentage |
|---|---|
| Stage 1 | |
| Water | 8.00 |
| Xanthan gum (Keltrol F) | 0.24 |
| Stage 2 | |
| Water | 71.52 |
| Texturizing Agent | 5.34 |
| Granulated Sucrose | 4.00 |
| Polydextrose | 3.28 |
| Vinegar (50 grain) | 2.67 |
| Modified Starch (Ultra Tex 4) | 2.06 |
| Salt | 1.95 |
| β-carotene (4.6% aq. susp. of 1% powder) | 0.36 |
| Mustard Flour (Durkee-French) | 0.24 |
| Tri-Sodium Citrate | 0.12 |
| Lactic Acid (884 solution) | 0.12 |
| Sodium Benzoate | 0.05 |
| Potassium Sorbate | 0.05 |
| Total | 100.00 |

The xanthan gum was hydrated separately by slowly adding to Stage 1 water while mixing to disperse.

Stage 2 water was preheated to 203° F. (95° C.) then added to a kitchen blender. The texturizing agent was slowly added while mixing on medium speed. Once dispersed, the mixture was mixed at high speed until uniformly smooth and dispersed.

The hydrated xanthan gum was added to the mixture and the entire mix was blended on high speed until uniform. The remaining dry ingredients were added to the bowl of a KITCHEN AID® (or equivalent) mixer. While mixing with the flat paddle attachment (speed 2), the hydrated texturizing agent/xanthan paste was added to the dries. The product was mixed until uniform, scraping sides with spatula as needed. The remaining wet ingredients were added with continued mixing. The paste was transferred to the bowl of a mini-food processor and mixed until smooth and homogeneous (about 2 to 3 minutes). The resulting product exhibited a smooth texture with a non-starchy, fat-like rheology.

In a control experiment a dry blend consisting of the individual components of the texturizing agent were added to the above formulation and processed as above. The resultant product was sensory attributed tested vs. the mayonnaise prepared with the texturizing agent. Results indicated that the complex was more fat-like in texture, less pasty and smoother in mouthfeel than the sample prepared with the individual ingredients.

EXAMPLE 8

Preparation of a Low-Fat Mousse Containing Texturizing Agent

The texturizing agent prepared according to Example 1 was incorporated into a chocolate mousse formulation. The resulting formulation produced a low-fat product that has a clean flavor, superior body and stability.

| Ingredients | Weight Percentage |
|---|---|
| Skim milk | 68.50 |
| Non-fat dry milk | 12.30 |
| Granulated sugar | 11.30 |
| Cocoa powder (13% fat) | 3.70 |
| Texturizing agent | 3.20 |
| Gelatin (30 mesh, 250 bloom) | 1.00 |
| TOTAL | 100.00 |

Milk was heated to 194° F. (90° C.) and transferred to a standard kitchen blender. All dry ingredients (including texturizing agent) were then slowly added to the hot milk while mixing on high speed. Once dry blend was uniformly dispersed, sample was mixed for an additional five more minutes. The mix was batch pasteurized by heating to 185° F. (85° C.) for 35 seconds, followed immediately with homogenization while hot [16,000 rpm for 2 minutes using a Polytron Homogenizer Model PT10/35 fitted with a PT205 generator (Brinkman Instruments, Westbury, N.Y.)]. Product was cooled to 40° F. (4° C.) and whipped in the bowl of KITCHEN AID® Mixer using the whisk attachment. Overrun is typically in the range of 80 to 100%. The finished product was smooth and exhibited a short fat-like texture.

EXAMPLE 9

Preparation of a Low-Fat Ranch Salad Dressing Containing Texturizing agent

A low-free spoonable dressing was prepared from the texturizing agent prepared in Example 1, using the following formula:

| Ingredients | Weight Percentage |
|---|---|
| Water to | 100.00 |
| Texturizing agent | 2.50 |
| Corn syrup | 25.00 |
| Skim butter milk solids | 5.60 |
| Liquid soybean oil | 1.60 |
| Salt | 1.00 |
| Lemon juice conc | 0.50 |
| Garlic juice | 0.25 |
| Xanthan gum (Keltrol F) | 0.30 |
| Monosodium glutamate | 0.10 |
| Lactic acid (88% solution) | 0.50 |
| Potassium sorbate | 0.05 |
| Sodium benzoate | 0.05 |
| TOTAL | 100.00 |

Water and corn syrup were preheated to 212° F. (100° C.) and placed in a kitchen blender. Texturizing agent was added to the solution while mixing on medium speed. Once dispersed, sample was mixed on high speed for 5 minutes. Remaining dry solids (as a dry blend) were added to above mixture and mixed until evenly dispersed. Oil and garlic juice were added and mixed to disperse. Contents were transferred to a beaker and product was cooled to room temperature while mixing with an overhead stirrer (200–300 rpm). Sour cream and acidulant were then slowly mixed in until evenly dispersed. The finished dressing exhibited a desirable body with a fat-like sensory yield stress.

In a control experiment a dry blend consisting of the individual components of the texturizing agent were added to the above formulation and processed as above. The resultant product was sensory attributed tested vs. the dressing prepared with the texturizing agent. The formulation with the complex was more fat-like in texture, less starchy and smoother in mouthfeel than the sample prepared with the individual ingredients.

EXAMPLE 10

Preparation of a No-Fat Margarine-Like Spread Containing Texturizing Agent

A fat-free spread was prepared from the texturizing agent prepared according to Example 1 using the following formula:

| Ingredient | Weight Percentage |
|---|---|
| Water to | 100.00 |
| Maltodextrin (GPC M040) | 20.00 |
| Xanthan gum (Keltrol F) | 0.20 |
| Texturizing Agent | 4.40 |
| Lecithin | 0.10 |
| Corn Syrup Solids (GPC M200) | 3.30 |
| Gelatin (Hormel P-8,250 Bloom) | 0.40 |
| Salt | 1.00 |
| TOTAL | 100.00 |

Water was heated to 93° C. (200° F.) then placed in a kitchen blender. Lecithin was added and dispersed while mixing on low speed, followed by the slow addition of the texturizing agent powder. Once dispersed, sample was mixed on high speed for 5 minutes. Mixture was transferred to a metal beaker and placed in a 82° C. (180° F.) (minimum) water bath. Sample was mixed with an overhead stirrer while adding dry blend (corn syrup solids, salt, xanthan, gelatin). Once dispersed, the remaining dry ingredients were added, all the while mixing slowly to aid dispersion. Product was heated for 20 minutes while maintaining the temperature between 82°–93° C. (180°–200° F.) with slow continuous mixing.

The finished product exhibited the texture and spreadability comparable to a full-fat margarine. The product was opaque and smooth in texture with a fat-like sheen.

EXAMPLE 11

Preparation of a Low-Fat Mayonnaise Containing Texturizing Agent Without Added Titanium Dioxide A low-fat mayonnaise was prepared with the texturizing agent produced in Example 5 using the following formula:

| Ingredients | Weight Percentage |
|---|---|
| Stage 1 | |
| Water | 6.19 |
| Xanthan gum (Keltrol F) | 0.21 |
| Stage 2 | |
| Water to | 100.00 |
| Texturizing Agent | 4.26 |
| Granulated Sucrose | 3.10 |
| Polydextrose | 5.07 |
| Vinegar (50 grain) | 2.03 |
| Frozen Egg Yolk | 1.65 |
| VERI-LO ® 100 (Pfizer) | 6.50 |
| Modified Starch (Ultra Tex 4) | 1.53 |
| Salt | 1.55 |
| β-carotene (1.2% aq. susp. of 1% powder) | 1.53 |
| Mustard Flour (Durkee-French) | 0.19 |
| Tri-Sodium Citrate (ADM) | 0.10 |
| Lactic Acid (88% solution) | 0.10 |
| Total | 100.00 |

The xanthan gum was hydrated separately by slowly adding to stage 1 water while mixing to disperse. Stage 2 water was preheated to 203° F. (95° C.) then added to a kitchen blender. The texturizing agent was slowly added while mixing on medium speed. Once dispersed, the mixture was mixed at high speed until uniformly smooth and dispersed. The hydrated xanthan gum was added to the mixture and the entire mix was blended on high speed until uniform. The remaining dry ingredients were added to the bowl of a KITCHEN AID® (or equivalent) mixer. While mixing with the flat paddle attachment (speed 2), the hydrated texturizing/xanthan paste was added to the dries. The product was mixed until uniform, scraping sides with spatula as needed. The remaining wet ingredients were added with continued mixing. The paste was transferred to the bowl of a mini-food processor and mixed until smooth and homogeneous (about 2 to 3 minutes). Resultant product was smooth in texture with a fat-like rheology.

In a control experiment the texturizing agent was removed from the mayonnaise formulation and replaced with the standard starch-based texturizing agent (prepared without xanthan or titanium). The resultant product was sensory attribute tested vs. the mayonnaise prepared with the texturizing agent. Data indicated the complex was less pasty and smoother in mouthfeel than the sample prepared with the standard texturizing agent.

EQUIVALENTS

Those skilled in the art will recognize, or be able to ascertain using no more than routine experimentation, many equivalents to the specific embodiments of the invention described herein. Such equivalents are intended to be encompassed by the following claims:

We claim:

1. A method for preparing a starch-based texturizing agent containing an insoluble microparticle and a gum in the form of in the form of a complex in which the insoluble microparticle is incorporated into a starch/gum matrix, comprising the steps of:
   a) heating a slurry of high amylose starch in an acidic aqueous medium at a temperature, pressure and time sufficient to substantially disrupt starch granules, to produce a solubilized starch solution;
   b) filtering the solubilized starch solution to remove impurities; and
   c) adding an insoluble microparticle and a gum to the filtered starch solution under agitating conditions, thereby producing a starch-based texturizing agent in the form of a complex in which the insoluble microparticle is incorporated into a starch matrix.

2. The method of claim 1 wherein the high amylose starch is derived from corn, oats, barley or pea.

3. The method of claim 1 wherein the slurry comprises from about 1 to about 30% (w/v) high amylose starch.

4. The method of claim 3 wherein the slurry comprises from about 5 to about 15% (w/v) high amylose starch.

5. The method of claim 1 wherein the insoluble microparticle is selected from the group consisting of titanium dioxide, aqueous insoluble organic or inorganic compounds, microcrystalline cellulose, whey proteins and prolamines.

6. The method of claim 5 wherein the insoluble microparticle is titanium dioxide and is added in an amount of from about 2 to about 25% by weight.

7. The method of claim 6 wherein the amount of titanium dioxide is about 3% by weight.

8. The method of claim 5 wherein the insoluble microparticle is added in an amount of from about 5 to about 50% by weight.

9. The method of claim 1 wherein the gum is selected from the group consisting of xanthan gum, gum arabic, carrageenan, locust bean gum, guar gum and combinations thereof.

10. The method of claim 9 wherein the gum is xanthan gum and is added in an amount of from about 2 to about 10% by weight.

11. The method of claim 10 wherein the amount of xanthan gum is from about 5 to about 6% by weight.

12. The method of claim 1, wherein the solution in step a) is treated with diatomaceous earth and activated charcoal before filtering in step b).

13. The method of claim 1, wherein step b) is performed by combining the solution with diatomaceous earth and filtering the combination through a carbon impregnated filtration device.

14. The method of claim 1, wherein step a) is performed by jet cooking the slurry of starch.

15. The method of claim 1 wherein the slurry has a pH of from about 3 to about 7.

16. The method of claim 15 wherein the pH is from about 4.3 to about 4.7.

17. The method of claim 1 further comprising
   reducing the temperature of the starch solution produced in step (c) to a temperature and for a period of time sufficient for the starch to partially or fully retrograde.

18. The method of claim 17 further comprising drying the texturizing agent into a powder.

19. The method of claim 1 wherein an excipient and/or additive is added prior to or after the filtration step.

20. The method of claim 19 wherein the excipient and/or additive is selected from the group consisting of maltodextrin, sugars, proteins, lipids, flavors, gums, hydrocolloids, colors and starches.

21. A method for preparing a starch-based texturizing agent containing titanium dioxide and xanthan gum in the form of a complex in which titanium dioxide particles are incorporated into a starch/xanthan gum matrix, comprising the steps of:
   a) heating a slurry of high amylose starch in an acidic aqueous medium at a temperature, pressure and time sufficient to substantially disrupt starch granules, to produce a solubilized starch solution;
   b) filtering the solubilized starch solution to remove impurities;
   c) adding titanium dioxide and xanthan gum to the filtered starch solution to thereby form a starch-based texturizing agent in the form of a complex in which titanium dioxide particles are incorporated into a starch/xanthan gum matrix; and
   d) drying the starch-based texturizing agent.

22. The method of claim 21 further comprising adding maltodextrin prior to or after the filtration step.

23. A starch-based texturizing agent comprising high amylose starch, an insoluble microparticle and a gum in the form of a complex in which the insoluble microparticle is incorporated into a starch/gum matrix.

24. A starch-based texturizing agent comprising pregelatinized high amylose starch, titanium dioxide and xanthan gum in the form of a complex in which titanium dioxide particles are incorporated into a starch/xanthan gum matrix.

25. A food formulation containing a starch-based texturizing agent comprising high amylose starch, an insoluble microparticle and a gum in the form of a complex in which the insoluble microparticle is incorporated into starch/gum matrix.

26. The food formulation of claim 25 wherein the food is selected from the group consisting of mayonnaise, salad dressings, edible spreads, sour cream, yogurt, cottage cheese dressing, ice cream, frozen desserts, mousse, cream cheese, processed cheese and whipped cream.

27. The food formulation of claim 25 wherein the starch is a pregelatinized high amylose starch, the insoluble microparticle is titanium dioxide and the gum is xanthan gum.

28. The food formulation of claim 26 that contains a reduced fat content or that is fat free.

29. A spread containing a starch-based texturizing agent comprising high amylose starch, an insoluble microparticle and a gum in the form of a complex in which the insoluble microparticle is incorporated into a starch/gum matrix.

30. The spread of claim 29 that contains a reduced fat content or that is fat free.

31. The method of claim 18 wherein the drying into a powder is performed by spray drying.

* * * * *

UNITED STATES PATENT AND TRADEMARK OFFICE
CERTIFICATE OF CORRECTION

PATENT NO. : 5,614,243
DATED : March 25, 1997
INVENTOR(S) : John M. Dunn and Eugene T. Finocchiaro It is certified that error appears in the above-indentified patent and that said Letters Patent is hereby corrected as shown below:

Column 19, line 36, Claim 1, line 3, after "of", delete
---in the form of---.

Signed and Sealed this

Twenty-third Day of September, 1997

Attest:

BRUCE LEHMAN

Attesting Officer    Commissioner of Patents and Trademarks